US007108549B2

(12) United States Patent
Lyu et al.

(10) Patent No.: US 7,108,549 B2
(45) Date of Patent: Sep. 19, 2006

(54) MEDICAL ELECTRICAL CONNECTOR

(75) Inventors: Suping Lyu, Maple Grove, MN (US); Thomas C. Bischoff, Minneapolis, MN (US); James T. Gates, Maple Grove, MN (US); Peter B. McIntyre, Mounds View, MN (US); Scott J. Robinson, Forest Lake, MN (US); Bruce R. Mehdizadeh, Savage, MN (US); James M. Iknayan, Andover, MN (US); Elisabeth L. Belden, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/812,796

(22) Filed: Mar. 30, 2004

(65) Prior Publication Data

US 2005/0221671 A1 Oct. 6, 2005

(51) Int. Cl.
*H01R 13/40* (2006.01)
*A61N 1/372* (2006.01)

(52) U.S. Cl. .......................... 439/587; 607/37; 607/38

(58) Field of Classification Search ................ 439/587, 439/909; 607/37, 38
See application file for complete search history.

(56) References Cited

U.S. PATENT DOCUMENTS 4,898,173 A 2/1990 Daglow et al.
4,922,607 A 5/1990 Doan et al.
4,944,088 A 7/1990 Doan et al.
5,007,435 A 4/1991 Doan et al.
5,843,141 A * 12/1998 Bischoff et al. .............. 607/37
6,026,567 A 2/2000 Swoyer et al.
6,167,314 A * 12/2000 Fischer et al. .............. 607/119
6,244,882 B1 * 6/2001 Greenstein .................. 439/205
6,501,990 B1 12/2002 Sundberg et al.
6,895,276 B1 * 5/2005 Kast et al. .................... 607/37
2003/0163171 A1 8/2003 Kast et al.

OTHER PUBLICATIONS

"Active Implantable Medical Devices—Four-Pole Connector System for Implantable Cardiac Rhythm Management Devices," PAC/CTF-N151R5 WD, p. i-58, AAMI (2000).

Belden, L., Memo, "Medtronic Quadripolar IS-4 Proposal," Association for the Advancement of Medical Instrumentation, Pacemaker Committee, Connector Task Force—IS-4 Team, PAC/CTF-N135, p. 1-6 (Sep. 18, 2000).

Meeting minutes, Association for the Advancement of Medical Instrumentation, Pacemaker Committee, Connector Task Force—IS-4 Team Teleconference, PAC/CTF-N137, p. 1-2 (Sep. 21, 2000).

Meeting minutes, Association for the Advancement of Medical Instrumentation, Pacemaker Committee, Connector Task Force—IS-4 Team Teleconference, PAC/CTF-N152, p. 1-2 (Nov. 30, 2000).

* cited by examiner

*Primary Examiner*—James R. Harvey
(74) *Attorney, Agent, or Firm*—Michael C. Soldner; Girma Wolde-Michael

(57) ABSTRACT

A connector terminal of a medical electrical lead or adapter includes a strut member supporting at least one electrical contact element and at least one seal zone element, which is positioned adjacent to the contact element.

89 Claims, 14 Drawing Sheets

MEDICAL ELECTRICAL CONNECTOR

TECHNICAL FIELD

The present invention relates to medical electrical leads and adapters and more particularly to connector terminals, which mate the leads and adapters with medical devices.

BACKGROUND

A host of medical devices include a connector bore into which a connector terminal of an electrical lead, or catheter, is inserted in order to make electrical connection with the device so as to form a medical system. Each insulated conductor, extending within a body of the lead, couples a lead electrode and or other electrically activated sensor to an electrical contact element formed on the connector terminal, and each contact element is engaged by a contact within the device connector bore when the connector is fully inserted within the bore.

Each electrical connection, between contact and contact element, within the bore must be isolated from another, and from the environment outside the bore, so that the connector terminal typically includes sealing rings positioned in between each contact element and at a distal end of the connector. The sealing rings deform upon insertion of the connector terminal into the bore and sealingly engage one or more internal surfaces of the bore when the connector terminal is fully inserted. Connector terminals conforming to IS-1 and DF-1 pacemaker industry standards are examples of connector terminals including sealing rings.

In an alternative configuration, sealing rings are included within a device connector bore rather than on the connector terminal; the rings within the bore sealingly engage one or more surfaces, or seal zones, on the connector terminal. It is desirable that connector terminals, for mating with such connector bores, be dimensionally stable both acutely and chronically so that both contact elements and seal zones are properly engaged with connector bore contacts and sealing rings, respectively, when the connector terminal is first fully inserted into the bore and then over the life of the coupling between the device and the lead.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION

The following detailed description is exemplary in nature and is not intended to limit the scope, applicability, or configuration of the invention in any way. Rather, the following description provides a practical illustration for implementing exemplary embodiments of the invention.

Figure 1:
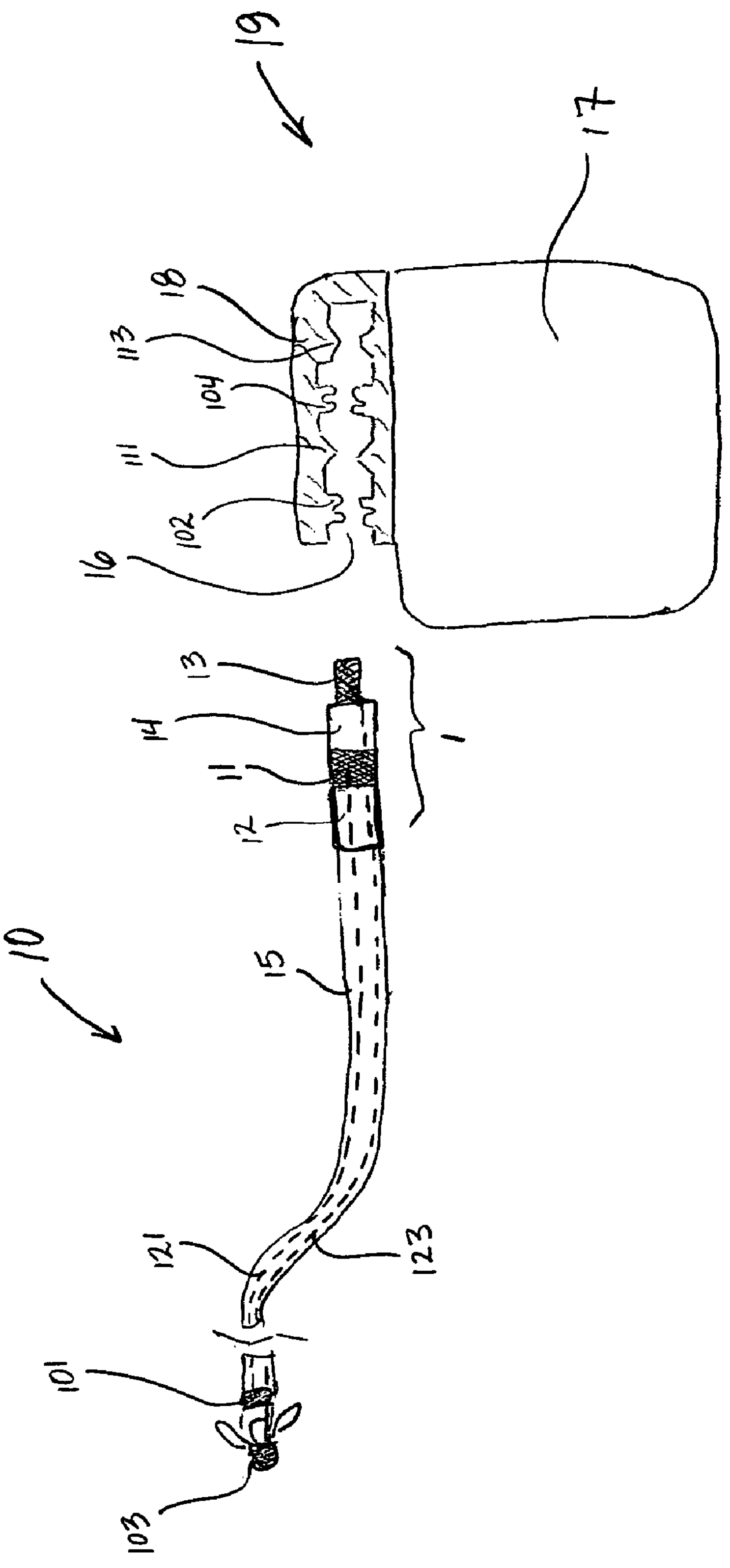
FIG. 1 is a schematic view with a partial section of a medical system, which may incorporate embodiments of the present invention.

FIG. 1 is a schematic view with a partial section of a medical system, which may incorporate embodiments of the present invention. FIG. 1 illustrates the system including an implantable medical electrical lead 10 and an implantable medical device (IMD) 19 adapted to mate with one another via insertion of a connector terminal 1 of lead 10 into a connector bore 16 of a device connector module 18. Upon full insertion of connector terminal 1 into bore 16, a first device electrical contact 111 engages a connector contact element 11 and a second device electrical contact 113 engages a connector pin 13 so that a pair of lead electrodes 101 and 103, coupled to a lead body 15, may sense and send electrical signals to device 19 from an implant site and deliver electrical stimulation from device 19 to the implant site. FIG. 1 illustrates a first elongate conductor 121 and a second elongate conductor 123 extending within lead body 15 to couple electrode 101 to connector contact element 11 and electrode 103 to connector pin 13, respectively; means for constructing implantable lead bodies including conductors and electrodes are well known to those skilled in the art. FIG. 1 further illustrates lead connector 1 including a first seal zone 12 and a second seal zone 14 positioned to be sealingly engaged by a first set of sealing rings 102 and a second set of sealing rings 104, respectively, when connector terminal 1 is full inserted within connector bore 16 of connector module 18. Means for constructing and incorporating connector modules into implantable medical devices are well known to those skilled in the art; one example of a connector module including connector bore sealing rings interspersed with contacts is described in co-pending patent application US20030163171.

Figure 2:
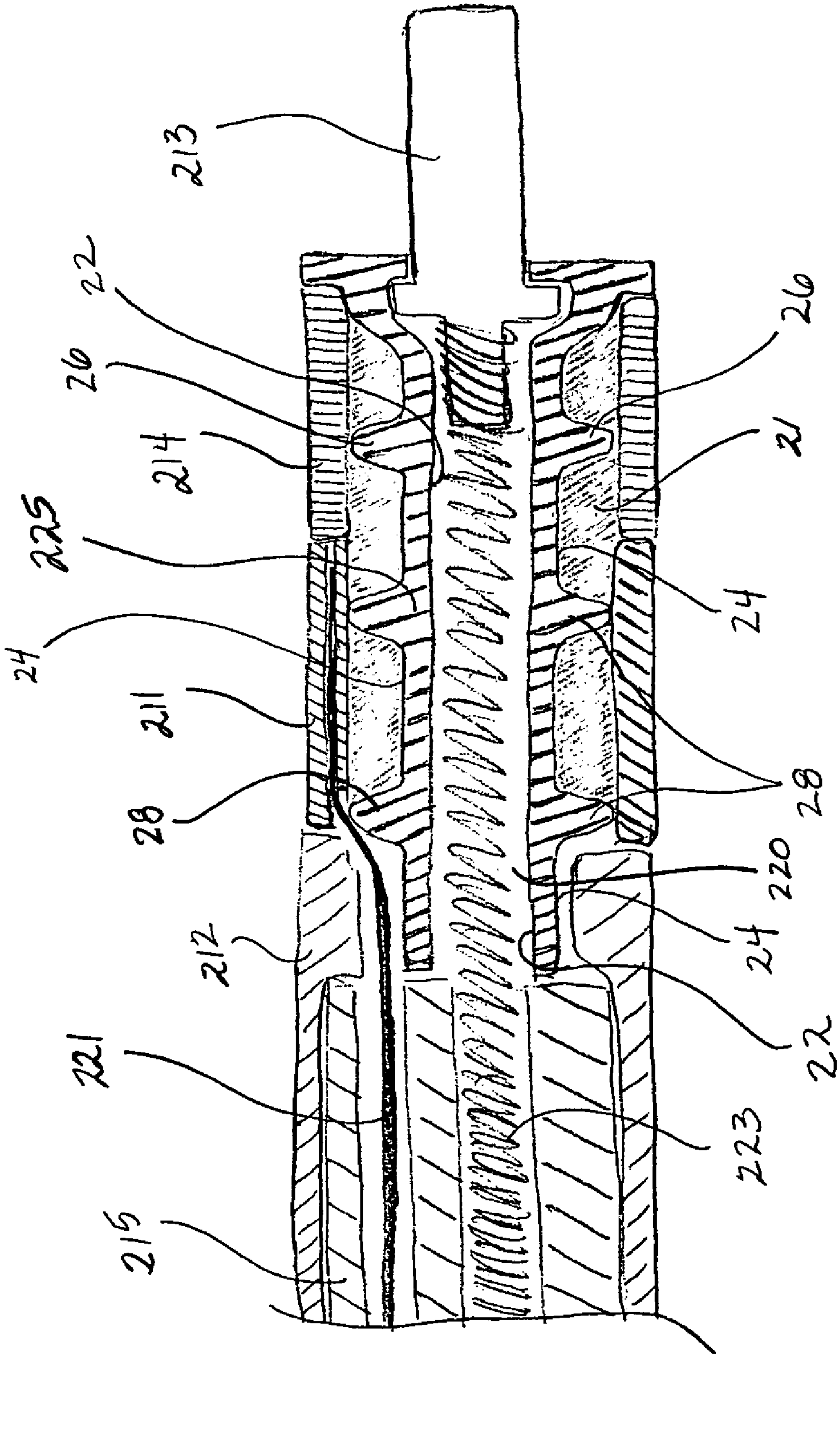
FIG. 2 is a longitudinal cross-section of a connector terminal according to one embodiment of the present invention.

FIG. 2 is a longitudinal cross-section of a connector terminal according to one embodiment of the present invention. FIG. 2 illustrates the connector terminal, for example terminal 1 shown in FIG. 1, including a strut member 225 supporting a contact element 211, on protrusions 28, and supporting a seal zone element 214, adjacent to, and approximately flush with, contact element 211, on protrusions 26; protrusions 28 and 26 extend from an outer surface 24 of strut 225 while an inner surface 22 of strut 225 forms a longitudinal lumen 220 extending therethrough. According to embodiments of the present invention, strut 225 is formed of at least one relatively rigid and insulative material(s), examples of which include, but are not limited to, polysulfone and harder grades of polyurethanes (i.e. 75D). FIG. 2 further illustrates a material 21, for example silicone medical adhesive, filling gaps between strut outer surface 24 and inner surfaces of contact element 211 and seal zone element 214.

According to further embodiments, materials forming seal zone element 214 include those resistant to scratching, for example by electrical contact clips (either those included within the device connector bore or those used externally, such as alligator clips), and those resistant to deformation over time under a pressure of connector bore sealing rings (i.e. sealing rings 104 illustrated in FIG. 1); such materials include but are not limited to harder plastics, for example polyetheretherketone (PEEK) or polysulfone, glass fiber-filled polymers and ceramics. An example of an appropriate glass fiber-filled polymer includes Elasthane 75D Polyurethane blended with Owens Corning milled glass fibers (737BC) having an average diameter of approximately 16 micrometers, a silane coating and a loading by weight ranging from approximately 2% to approximately 40%. Another example of a glass fiber-filled polymer includes Tecothane (TT-1075D-M, Thermedics Polymer Products, 207 Lowell Street, Wilmington, Mass. 01887) blended with chopped fiber glass (Chop Vantage 3540, PPG Industries, Inc., One PPG Place, Pittsburgh, Pa. 15272) having an average length of approximately 3.2 mm, an average diameter of approximately 10 micron, an organic sizing and a loading by weight ranging from approximately 2% to approximately 40%. Such composite materials are blended according to methods known to those skilled in the art, for example with a twin-screw extruder, and then molded into the form of seal zone elements.

Examples of appropriate ceramic materials include zirconia, alumina and sapphire. Zirconia and alumina may be molded and then machined to meet dimensional tolerances of seal zone elements, according to methods known to those skilled in the art. According to one embodiment of the present invention a ceramic seal zone element is joined to contact element 211, which may be formed from titanium or gold, at adjacent edges by means of brazing; brazing processes such as are common to electrical feedthrough assembly may be employed. According to alternate embodiments, contact element 211 may be formed of any other appropriate conductive and corrosion resistant materials known to those skilled in the art, for example MP35N alloy or stainless steel.

According to some embodiments of the present invention, seal zone element 214 includes an outer surface free of protrusions, since protrusions may compromise sealing between the surface and connector bore sealing rings; protrusions which may compromise sealing are those exceeding a height of approximately 0.002 inch or 0.003 inch.

FIG. 2 further illustrates a connector sleeve 212 coupling a lead body 215 to the connector, by means of an overlapping junction on lead body 215 and outer surface 24 of strut 225, and a cable conductor 221 extending from lead body 215, along strut outer surface 24, to couple with contact element 211. The illustrated embodiment also shows a coil conductor 223 extending from lead body 215 into strut lumen 220 to couple with a connector pin 213 engaged in a proximal end of strut lumen 220. Conductors 221 and 223, correspond to conductors 121 and 123 shown in FIG. 1 and are formed according to any appropriate means known to those skilled in the art and from any appropriate materials known to those skilled in the art, one example of which is an MP35N alloy.

Figure 3A:
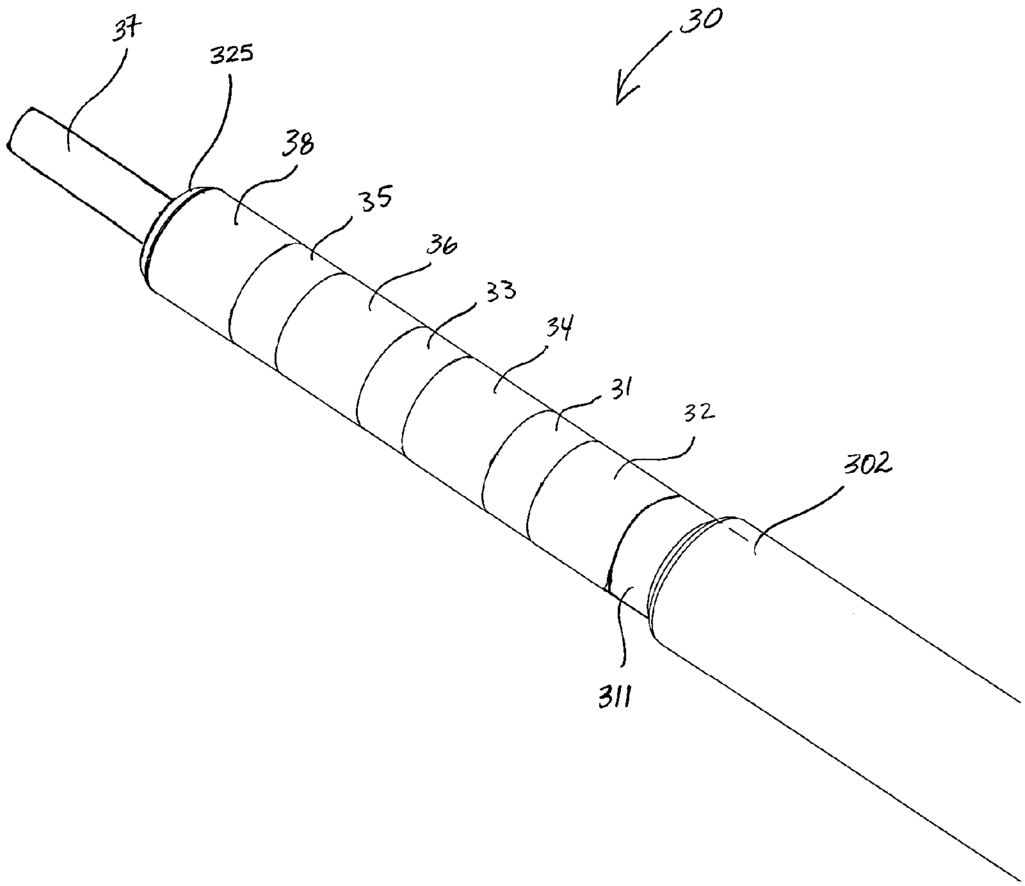
FIG. 3A is a perspective view of a connector terminal according to some embodiments of the present invention.
Figure 3B:
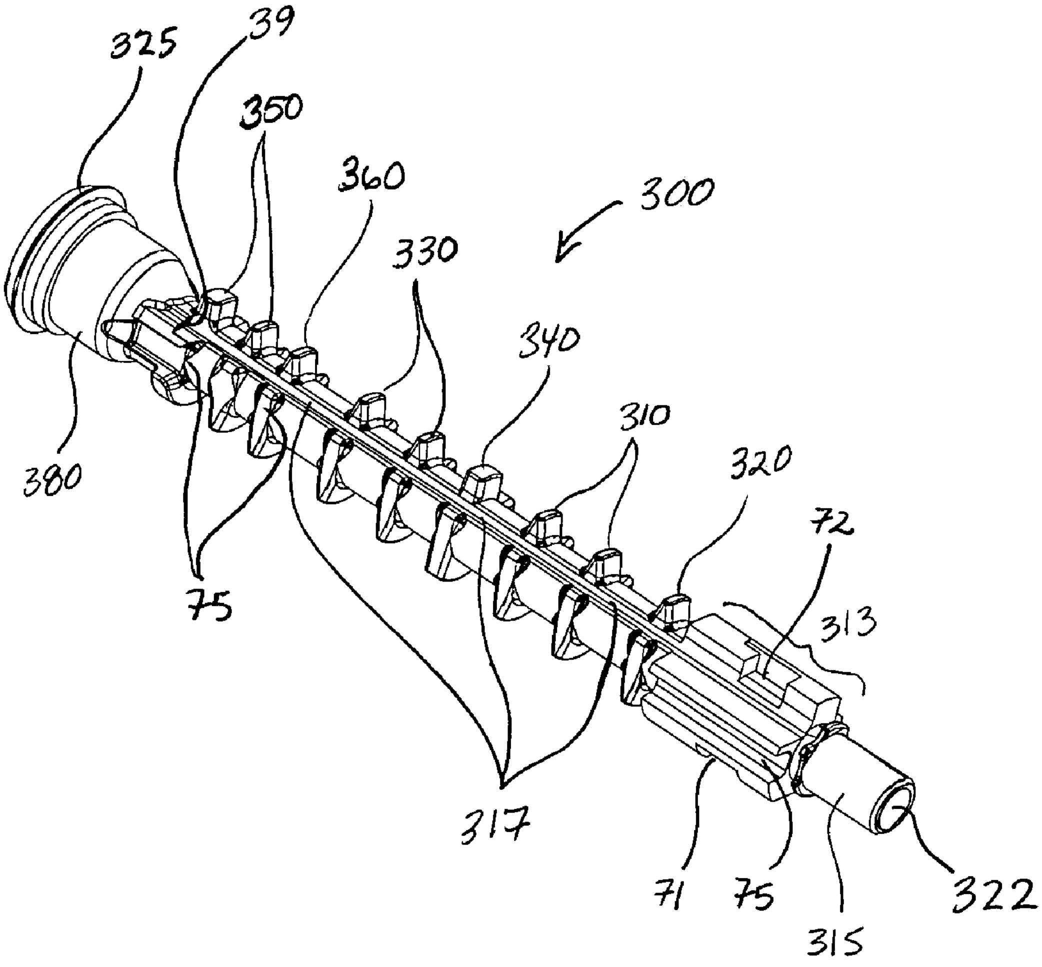
FIG. 3B is a perspective view of one component included in the connector terminal shown in FIG. 3A according to one embodiment of the present invention.

FIG. 3A is a perspective view of a connector terminal 30 and FIG. 3B is a perspective view of a strut member 300, included in connector terminal 30, according to one embodiment of the present invention. FIG. 3A illustrates connector terminal 30 including a connector pin 37, multiple contact elements 31, 33 and 35 and multiple seal zone elements 32, 34, 36 and 38; such a connector terminal would support a medical electrical lead including, for example, four independent electrodes such as those employed with internal cardioversion and defibrillation devices (ICD's), which include two defibrillation electrodes and a pair of pace/sense electrodes. According to some embodiments of the present invention, all seal zone elements 32, 34, 36 and 38 are formed of one of the materials described above (for seal zone element 14 of FIG. 2); according to alternate embodiments, one or more of each seal zone elements 32, 34, 36 and 38 is formed of a different material from the rest. According to an exemplary embodiment of the present invention each seal zone element 32, 34, 36 and 38 has an outer diameter of approximately 0.126 inch and an overall length of approximately 0.113 inch; and contact elements 31, 33 and 35 have a maximum outer diameter of approximately 0.126 inch and an exposed length of approximately 0.063 inch.

Figure 6:
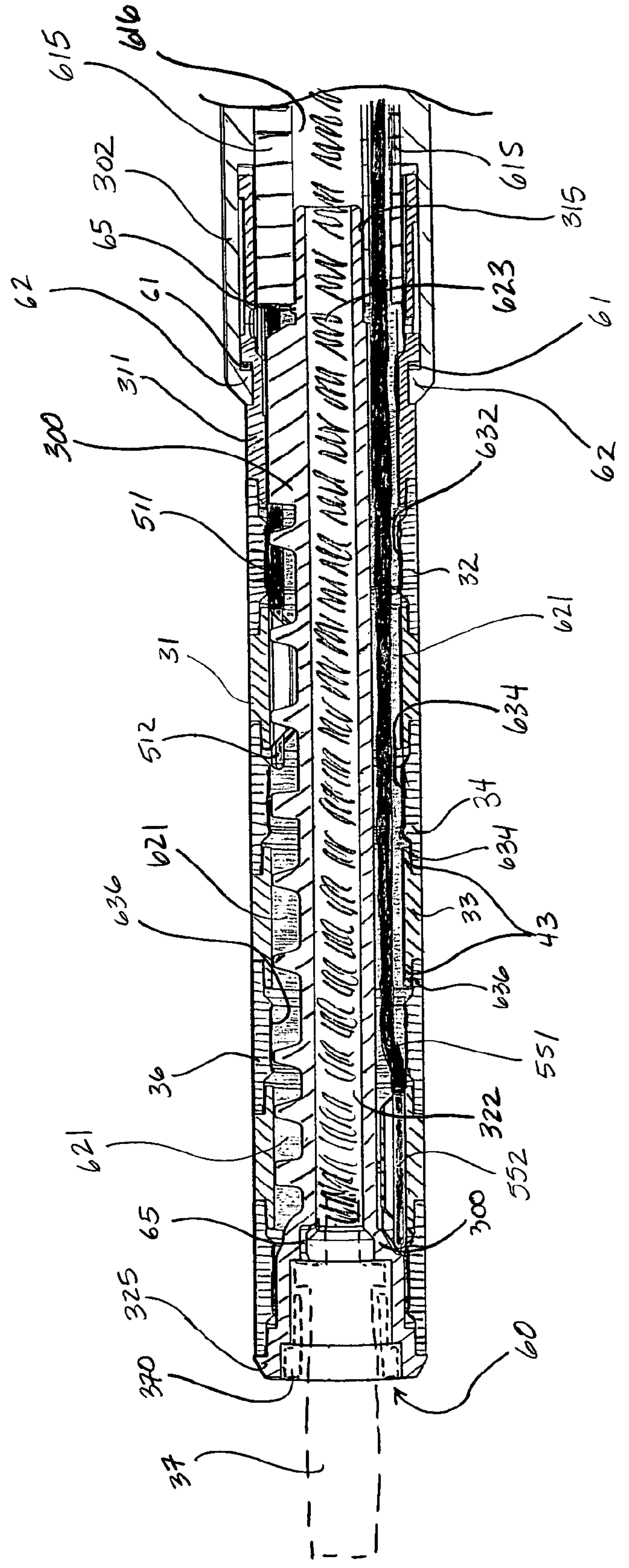
FIG. 6 is a longitudinal cross-section of a portion of the connector terminal shown in FIG. 3A.

FIG. 3B illustrates strut 300 (in the same perspective as connector 300 in FIG. 3A), which supports contact elements 31, 33 and 35, on protrusions 310, 330 and 350, and seal zone elements 32, 34, 36 and 38, on protrusions 320, 340, 360 and 380; similar to strut 225 illustrated in FIG. 2, each protrusion 310, 320, 330, 340, 350, 360, and 380 extends from an outer surface of strut 300 and an inner surface of strut 300 forms a longitudinal lumen 322 extending therethrough (refer also to FIG. 6).

FIG. 3A in conjunction with FIG. 3B further illustrate connector 30 including an end cap 311 which is mounted on a portion 313 of strut 300 in order to urge contact elements 31, 33 and 35 and seal zone elements 32, 34, 36 and 38 against one another and against a stop 325 formed at an opposite of strut 300; portion 313 includes locking recesses 71 and 72 to fixedly engage an inner surface of cap 311, which will be described in greater detail in conjunction with FIGS. 7F and 8. FIG. 3B also illustrates a surface 315 at a distal end of strut, onto which a generally tubular lead body 615 (FIG. 6) may be mounted, and FIG. 3A illustrates a connector sleeve 302, which overlays lead body 615 and end cap 311 (FIG. 6).

Figure 4:
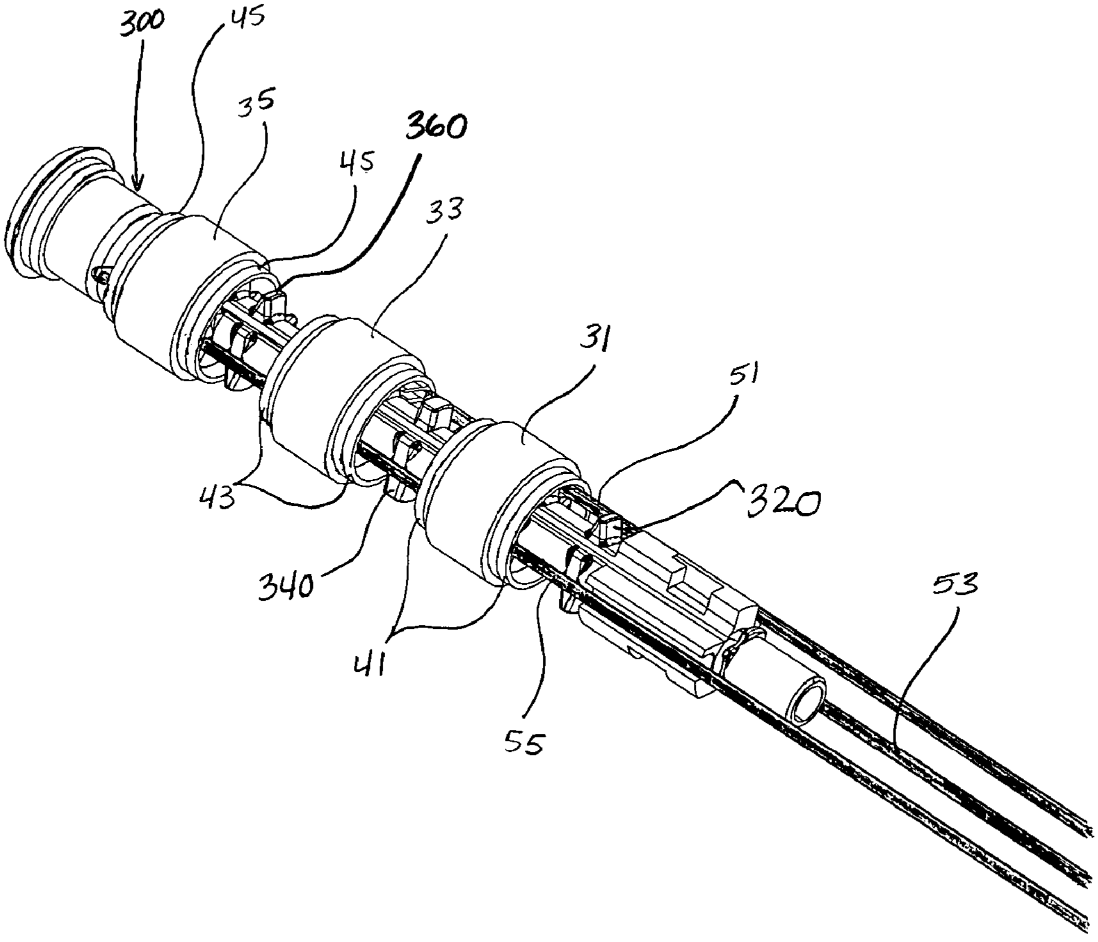
FIG. 4 is the same perspective view of the connector terminal shown in FIG. 3A wherein only certain components are shown.

FIG. 3B further illustrates a first conductor channel 75 extending along an outer surface of strut 300, cutting through protrusions 310, 320, 330, 340, 350 and 360. FIG. 4 is a perspective view of the connector terminal shown in FIG. 3A wherein only contact elements 31, 33 and 35 and their associated conductors 51, 53 and 55, respectively, are shown to illustrate a routing of conductors 51, 53 and 55 along the outer surface of strut 300. According to embodiments of the present invention, just as first channel 75 extends through protrusions 310, 320, 330, 340, 350 and 360 holding conductor 55, a second channel extends at least through protrusions 310, 320, 330 and 340 to hold conductor 53 and a third channel extends at least through protrusions 310 and 320 to hold conductor 51; the channels are positioned spaced apart from one another, about a circumference of the strut, to isolate conductors 51, 53 and 55 from one another.

Figure 5B:
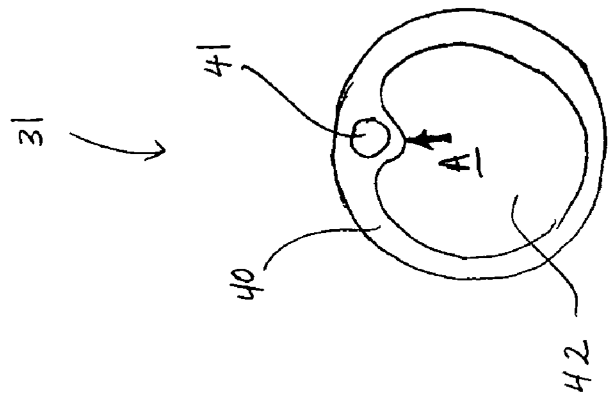
FIG. 5B is an end view of one component of the subassembly shown in FIG. 5A.
Figure 5A:
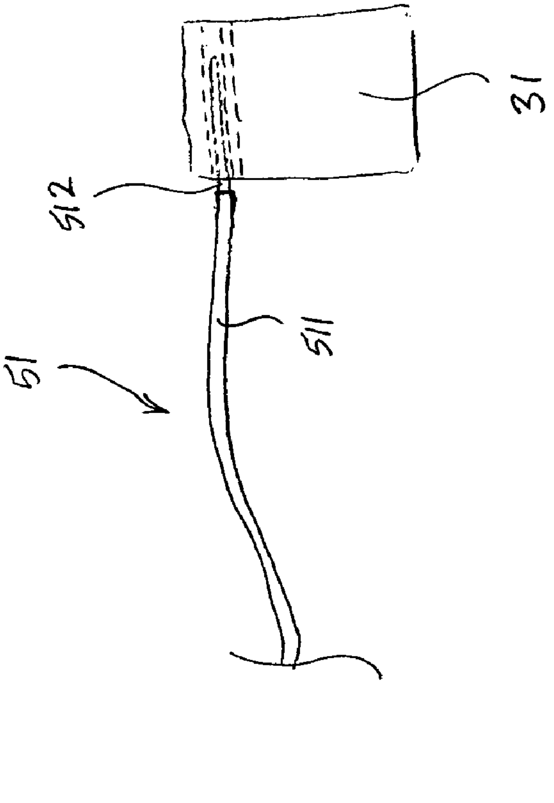
FIG. 5A is a plan view of a subassembly included in the connector terminal shown in FIG. 3A according to an embodiment of the present invention.

According to one embodiment of the present invention, cable conductors 51, 53 and 55 are coupled to contact elements 31, 33, and 35 within a feature formed on an internal surface of contact elements 31, 33, and 35; FIGS. 5A–B illustrate such an embodiment. FIG. 5A is a plan view of the subassembly of contact element 31 and conductor 51 and FIG. 5B is an end view of contact element 31. FIG. 5A illustrates conductor 51 including an outer insulative layer 511 which is stripped from an end 512 of conductor 51; end 512 is inserted into an eyelet 41, formed in sidewall 40 of contact element 31, and force directed, per arrow A, from an lumen 42 of contact element 31 crimps end 512 within eyelet 41 to electrically and mechanically couple conductor 51 to contact element 31. According to one embodiment, outer insulative layer 511 is a fluoropolymer coating, for example PTFE or ETFE.

FIG. 3B further illustrates strut 300 including a backfill channel 317 extending from surface 315, along strut outer surface, to an end point 39 in proximity to the proximal end of strut 300. According to one embodiment of the present invention, channel 317 provides a guide for a needle to enter beneath seal zone elements 32, 34, 36 and 38 and contact elements 31, 33 and 35 in order to dispense a backfill material between these elements and the outer surface of strut 300. FIG. 6 illustrates the connector including a backfill 621 and such a filling method will be described in greater detail in conjunction with FIG. 7E.

FIG. 6 is a longitudinal cross-section of a portion of the connector terminal shown in FIG. 3A. FIG. 6 illustrates each contact element 31, 33 and 35 including recessed outer surfaces extending from each end, for example surfaces 43 of contact element 33, so that a portion of an inner surface of each seal zone element 32, 34, 36 and 38 may overlap, for example inner surface 634 or seal zone element 34 and inner surface 636 of seal zone element 36; according to this embodiment of the present invention overlapping surfaces facilitate stable positioning of outer surfaces of seal zone elements 32, 34, 36 and 38 and contact elements 31, 33 and 35 flush with one another. According to some embodiments seal zone inner surfaces 632, 634 and 636 further include a surface treatment promoting adhesion with backfill material 621; according to one embodiment backfill material 621 is silicone medical adhesive and inner surfaces 632, 634 and 636 of seal zone elements 32, 34, and 36, formed of either a ceramic or a polysulfone undergo a siloxane plasma treatment. According to another ceramic embodiment, seal zone elements 32, 34, and 36 are hot heptane cleaned to enhance adhesion, and according to yet another ceramic embodiment, a forming operation for elements 32, 34, and 36 includes a clean fire step to enhance adhesion. Furthermore, according to some embodiments, outer insulative layers of conductors are treated for adhesion with backfill 621, for example layers 511 and 551 (of conductors 51 and 55), formed of a fluoropolymer, include a silane plasma treatment to enhance bonding with silicone medical adhesive as backfill 621.

The junction, according to one embodiment of the present invention, between lead body 615 and strut 300 is also shown in FIG. 6. FIG. 6 illustrates an inner surface of a lumen 616 of lead body 615 mounted on mounting surface 315 (FIG. 3B) of strut; strut end cap 311 extends over lead body 615 and connector sleeve 302, which is coupled to an outer surface of lead body 615, extends over end cap 311 such that a proximal edge 62 interlocks in a groove 61 of end cap 311. According to embodiments of the present invention end cap is formed of a rigid plastic, for example of a relatively hard grade of polyurethane or of a polysulfone, and sleeve 302 and lead body are formed of a more flexible polymer, for example of a softer grade of polyurethane or of silicone. Furthermore, lead body 615 and strut mounting surface 315, sleeve 302 and lead body 615, sleeve 302 and end cap 311 and end cap 311 and strut portion 313 may be joined by any appropriate means known to those skilled in the art, for example adhesively bonded or ultrasonically welded.

FIG. 6 further illustrates lumen 322 of strut 300 including a proximal portion 60, which according to one embodiment is enlarged to engage connector pin 37 and a pin retaining element 370 (both shown by dashed lines), which is bonded within strut 300 to hold pin 37 in place; as in FIG. 2, a conductor 623 extends from lead body 615 through lumen 322 to couple with pin 37. FIG. 6 also illustrates a keying feature 65 formed in lumen 322 in proximity to portion 60; according to one embodiment, keying feature 65 is used to orient strut 300 on an assembly pin 700 (FIG. 7A), which facilitates proper assembly of the connector terminal as will be described in conjunction with FIGS. 7A–F.

Figure 7A:
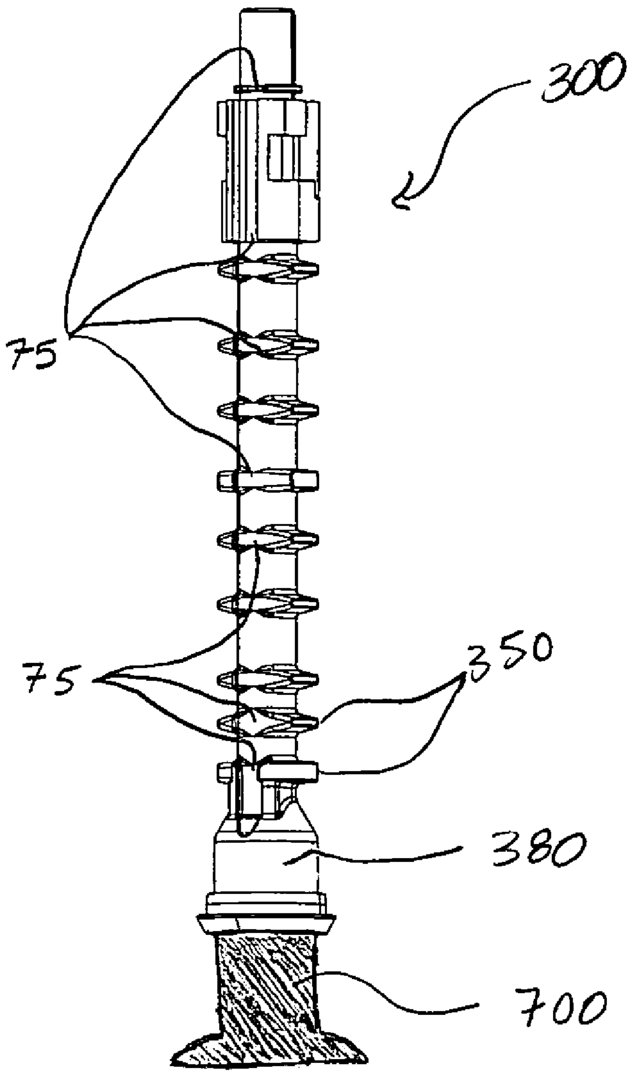
FIGS. 7A–E are plan views of a connector subassembly at successive stages of an assembly process according to one method of the present invention.
Figure 7B:
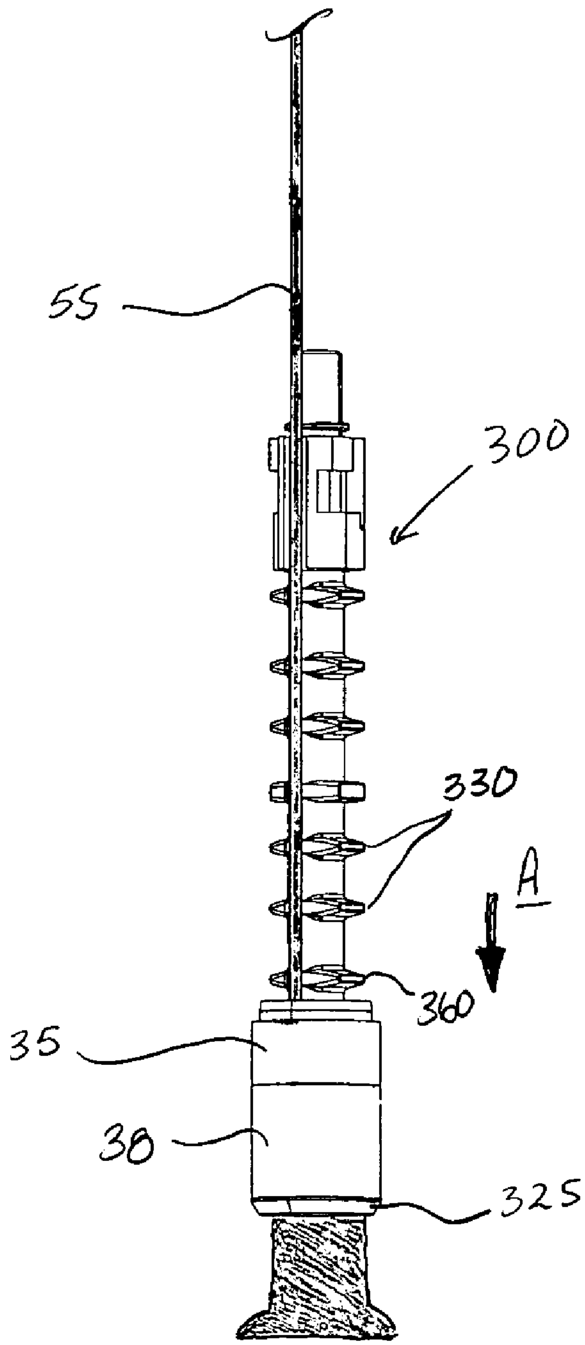
Figure 7C:
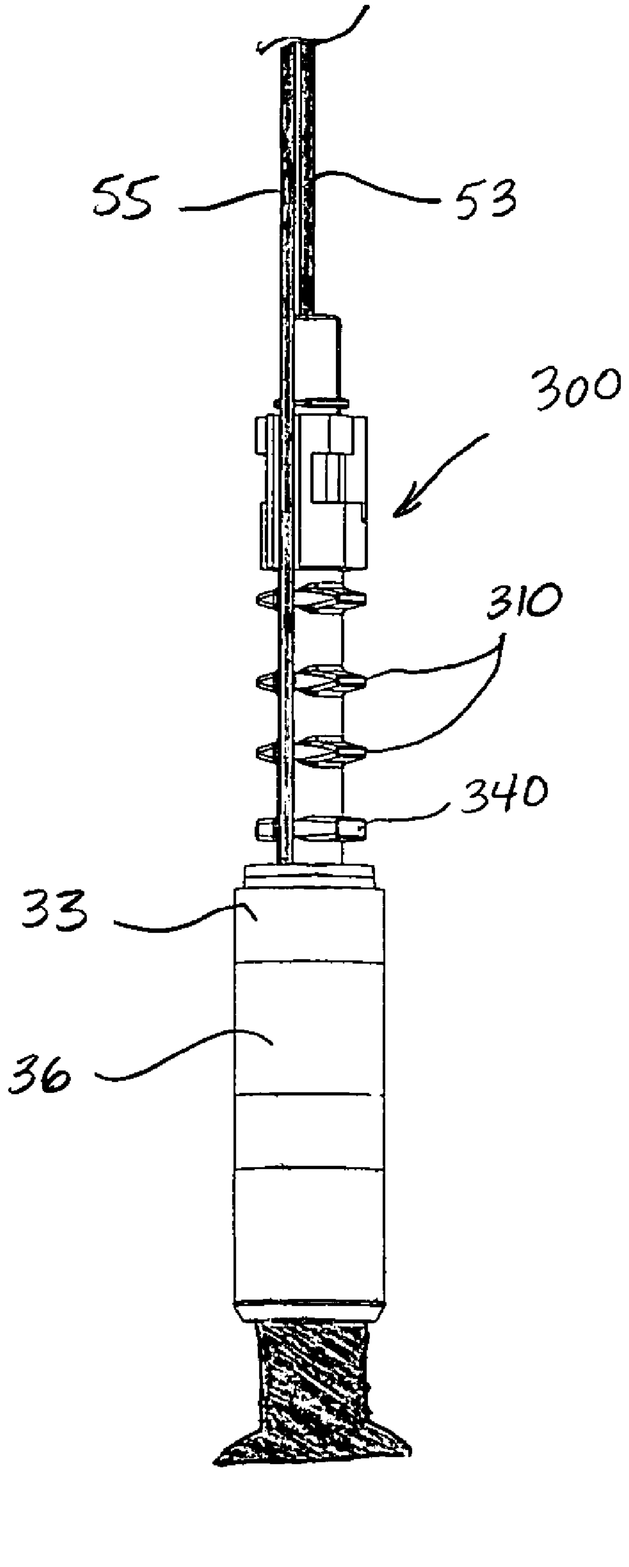
Figure 7D:
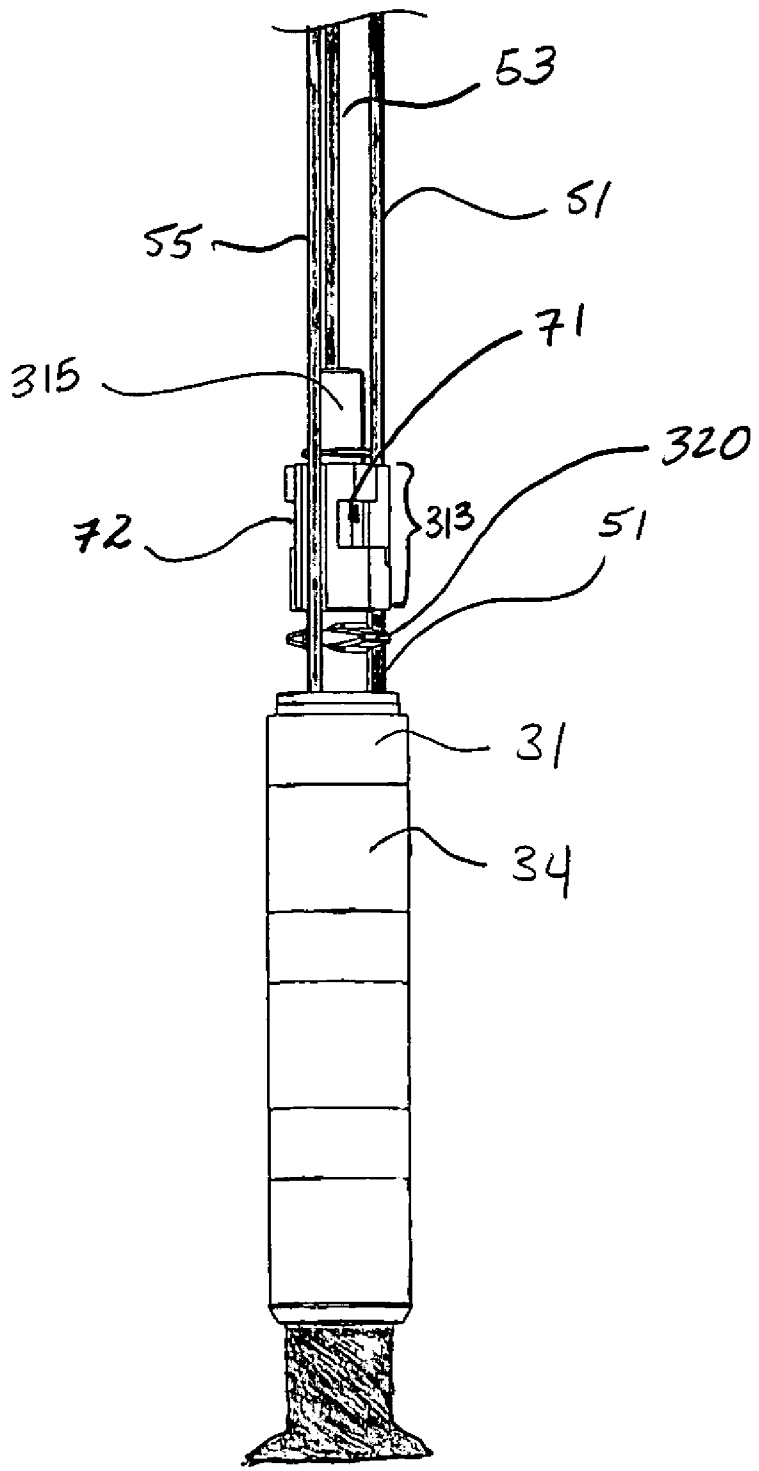
Figure 7E:
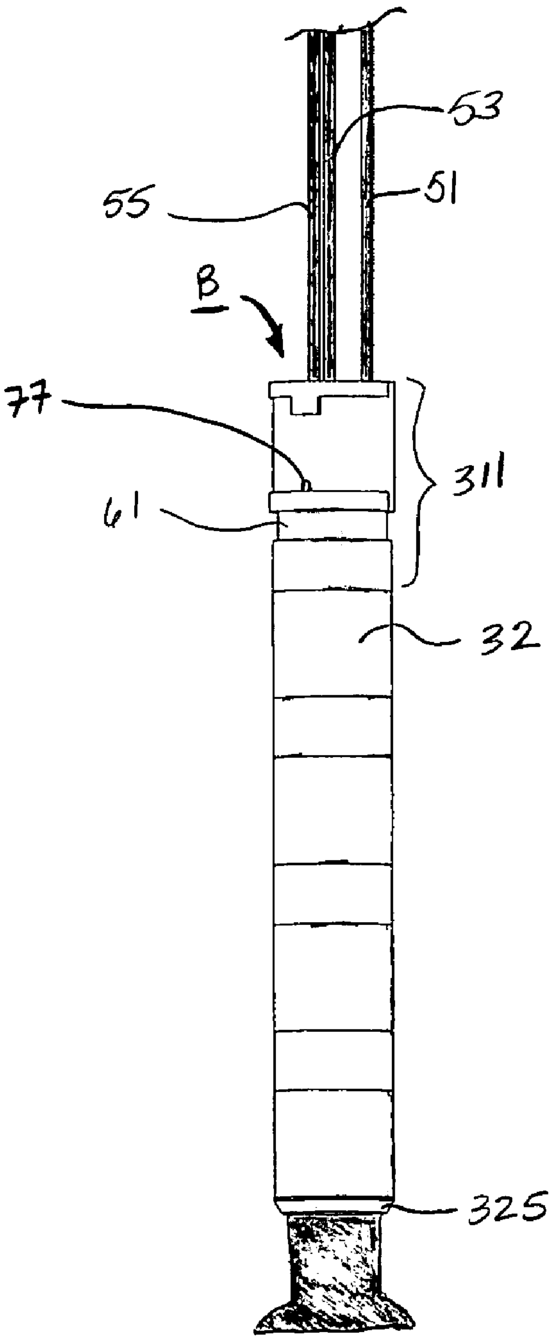
Figure 7F:
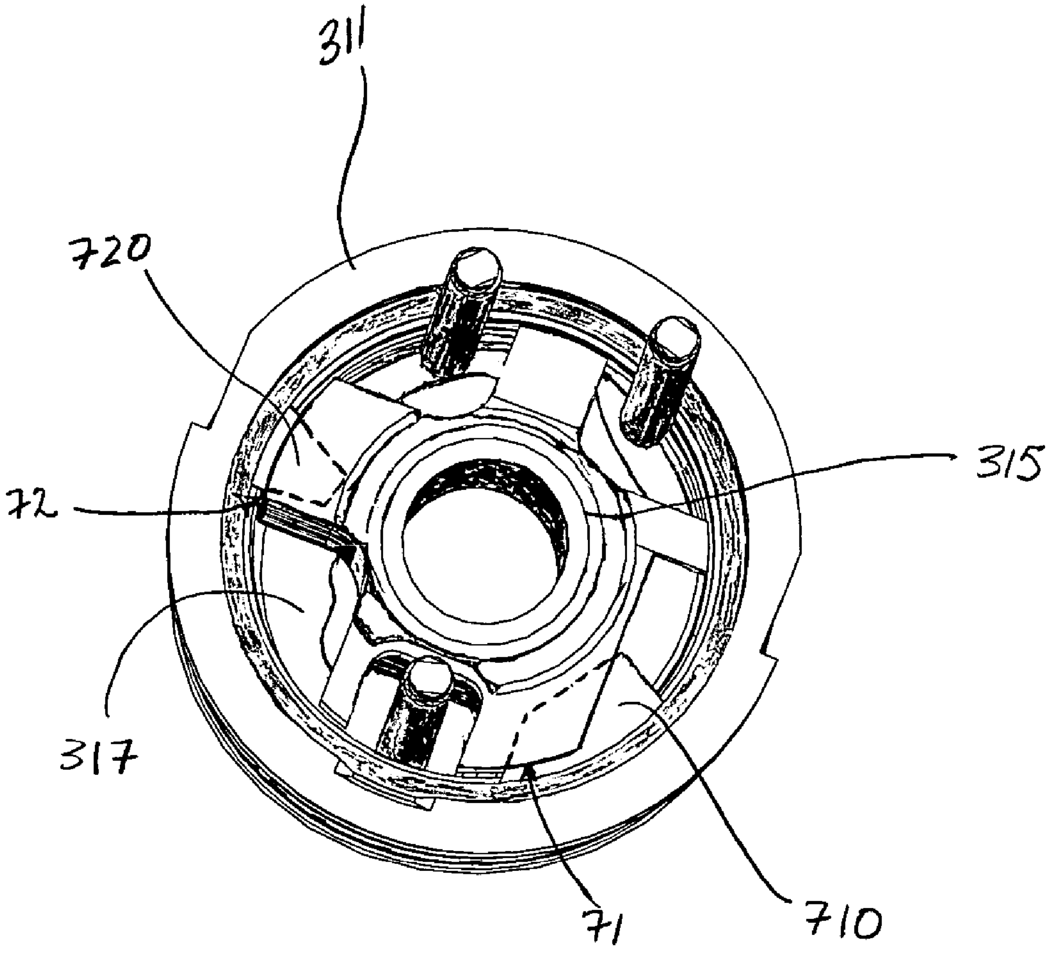
FIG. 7F is a perspective end view of the connector subassembly shown in FIG. 7E according to one embodiment of the present invention.
Figure 8:
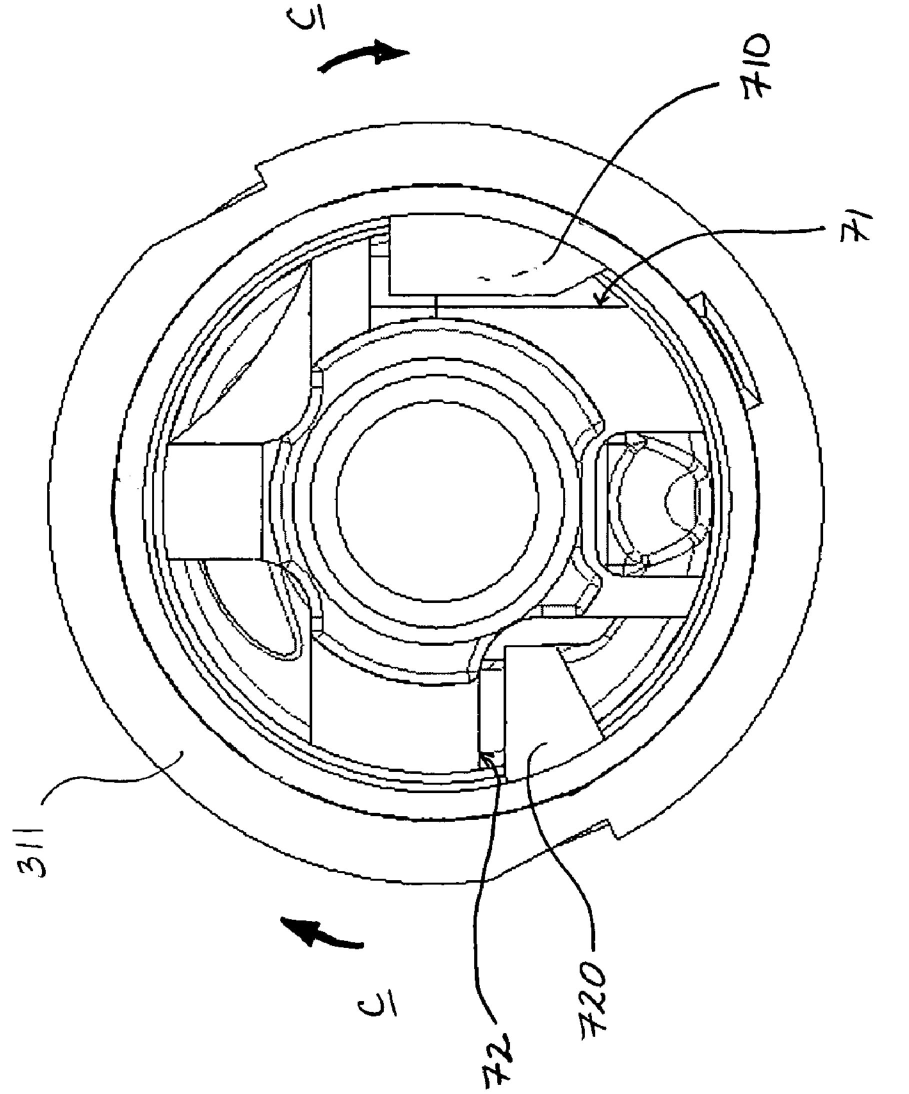
FIG. 8 is an end view of a portion of the connector subassembly shown in FIG. 7F detailing a component of the assembly according to one embodiment of the present invention.

FIGS. 7A–E are plan views of a connector subassembly at successive stages of an assembly process according to one method of the present invention; and FIG. 7F is a perspective end view of the connector subassembly shown in FIG. 7E according to one embodiment of the present invention. FIG. 7A illustrates strut 300 mounted on assembly pin 700 and FIG. 7B illustrates seal zone element 38 and contact element 35, which is coupled to conductor 55, having been mounted, successively or jointly, onto strut per arrow A. Conductor 55 may have been coupled to contact element 35 prior to assembly on strut 300, as previously described in conjunction with FIGS. 5A–B, or conductor 55 may have been coupled according to other means known to those skilled in the art, such as laser welding, either before assembly of contact element 35 onto strut or after assembly of contact element 35 onto strut; such is the case for each contact element assembled onto strut 300.

According to some embodiments of the present invention, strut 300 is molded from a relatively rigid and insulative material, for example 75D polyurethane or polysulfone. As is illustrated in FIGS. 7A–B, protrusion 380 supports seal zone element 38, protrusions 350 support contact element 35 and channel 75 allows passage of conductor 55 along the outer surface of strut 300, distally from contact element 35. Prior to assembling seal zone element 38 onto protrusion 380 a bead of adhesive may be dispensed on an inner surface of element 38 or on a surface of protrusion 380.

FIG. 7C illustrates seal zone element 36 and contact element 33, which is coupled to conductor 53, having been mounted, successively or jointly, onto strut per arrow A (FIG. 7B). As is illustrated in FIGS. 7B–C protrusion 360 supports seal zone element 36, protrusions 330 support contact element 33 and a channel on another side (not seen) of strut allows passage of conductor 53 along the outer surface of strut 300, distally from contact element 33.

FIG. 7D illustrates seal zone element 34 and contact element 31, which is coupled to conductor 51, having been mounted, successively or jointly, onto strut 300 per arrow A (FIG. 7B). As is illustrated in FIGS. 7C–D protrusion 340 supports seal zone element 34, protrusions 310 support contact element 31 and a channel (not seen) along a side of strut allows passage of conductor 51 along the outer surface of strut 300, distally from contact element 31.

FIG. 7E illustrates seal zone element 32 and end cap 311 having been mounted onto strut per arrow A (FIG. 7B). As is illustrated in FIGS. 7D–E protrusion 320 supports seal zone element 32 and strut portion 313 supports end cap 311. FIG. 7F is a perspective end view of the connector subassembly shown in FIG. 7E wherein locking recesses 71 and 72 engage internal protruding features 710 and 720, respectively, of cap 311. According to the illustrated embodiment cap 311 is mounted onto strut 300 by first sliding cap 311 over portion 313, per arrow A, so that internal protruding features 710 and 720 are longitudinally aligned with locking recesses 71 and 72 but circumferentially offset from recesses 71 and 72, as illustrated in FIG. 8. Then, to engage protruding features 710 and 720 in locking recesses 71 and 72, cap 311 is rotated, per arrow C (FIG. 8) until protruding features 710 and 720 'bottom out' circumferentially in locking recesses 71 and 72, at which point cap 311 is pushed per arrow A (FIG. 7B) to lock features 710 and 720 within recesses 71 and 72 so that end cap 311 is engaged on strut 300 holding seal zone elements 32, 34, 36 and 38 and contact elements 31, 33, and 35 in place. According to some embodiments, recesses 71 and 72 are dimensioned to provide some play allowing variances in length due to a tolerance stack up of seal zone elements 32, 34, 36 and 38 and contact elements 31, 33, and 35 on strut 300. Prior to assembling cap 311, adhesive may be applied in locking recesses 71 and 72.

FIGS. 7E and 7F further illustrate an assembly backfilling method according to one embodiment wherein a needle attached to a syringe filled with backfill material (not shown) is inserted, per arrow B, in between strut 300 and assembled seal zone elements 32, 34, 36 and 38, contact elements 31, 33, and 35 and end cap 311, along channel 317 (also shown in FIG. 3B). According to one embodiment, the needle is inserted such that a tip of the needle bottoms out against end point 39 (FIG. 3B) and is slowly withdrawn as backfill material 621 (FIG. 6) is dispensed; as illustrated in FIG. 7E, end cap 311 further includes a vent hole 77 facilitating release of air for a uniform fill. According to an exemplary embodiment an EFD HP-4X dispenser incorporating an XL1000 dispense valve and a 23 gauge thin-walled needle, approximately 0.925 inches long (equipment commercially available from EFD Inc. of East Providence Rhode Island) is used to dispense silicone medical adhesive at a dispensing pressure of approximately 70 psi. Following backfill, according to some embodiments, adjacent edges of seal zone elements 32, 34, 36 and 38 and contact elements 31, 33, and 35 are further joined together, for example by brazing, as previously described, or by adhesive bonding.

According to embodiments assembled per FIGS. 7A–E, final assembly steps encompass joining a lead body, i.e. body 615 shown in FIG. 6. Referring back to FIG. 6, conductor coil 623 extending proximally from lead body 615 is routed into lumen 322 of strut 300 and lead body lumen 616 is mounted on mounting surface 315; according to this embodiment, coil 623 may be stretched proximally out from strut proximal portion 60 to couple coil 623 to connector pin 37, for example, via welding or crimping, after which pin 37 is pushed into proximal portion 60 and secured there by means of retaining element 370 as previously described. According to one set of embodiments, cable conductors 51, 53 and 55 (FIG. 7E), are routed into other lumens of lead body 615 as coil conductor 623 is routed into strut lumen 322, and are of a length to extend from the connector assembly into lead body 615 to points where they are coupled to electrodes in subsequent steps of lead assembly; according to an alternate set of embodiments, conductors 51, 53 and 55 are of a shorter length and are thus each spliced, in proximity of connector sleeve 302, to conductors extending proximally through lead body 615 from lead electrodes in the subsequent steps of lead assembly.

For the purposes of this application, reference has been made only to a pacemaker type of an implantable medical device and lead, it being understood that any medical system may employ embodiments of connectors according to the present invention described herein. Furthermore, although the foregoing detailed description describes the invention with reference to specific embodiments, it may be appreciated that various modifications and changes can be made without departing from the scope of the invention as set forth in the appended claims. For example adapters, which include connector assemblies as described herein and are known by those skilled in the art for converting one type of lead connector to another type, are within the scope of the present invention.

What is claimed is:

1. A medical electrical lead comprising a connector terminal, the connector terminal adapted to mate with a medical device and comprising:

an electrical contact element;

a seal zone element positioned adjacent the contact element;

an elongate conductor extending from the proximal end of the lead into the connector where the conductor couples with the contact element; and a relatively rigid strut member completely formed from at least one electrically insulative material and including an outer surface and an inner surface, the inner surface forming a longitudinal lumen extending through the strut, a seal zone supporting protrusion extending from the outer surface of the strut member and upon which the seal zone element is mounted;

a contact supporting protrusion extending from the outer surface of the strut member, the contact supporting protrusion being longitudinally spaced apart from the seal zone supporting protrusion and upon which the contact element is mounted;

an adhesive backfill positioned beneath the seal zone element and the strut outer surface; and a longitudinal channel formed within the strut member facilitating application of the adhesive backfill from an end of the strut member.

2. The lead of claim 1, wherein at least one of the seal zone and contact supporting protrusions includes a channel through which the elongated conductor passes.

3. The lead of claim 1 wherein the seal zone element further includes an inner surface having a treatment promoting adhesion between the inner surface and the adhesive backfill.

4. The lead of claim 1, wherein an end of the strut includes a lead body-mounting surface.

5. A medical electrical lead comprising a connector terminal, the connector terminal adapted to mate with a medical device and comprising:

an electrical contact element;

a seal zone element positioned adjacent the contact element;

an elongate conductor extending from the proximal end of the lead into the connector where the conductor couples with the contact element; and a relatively rigid strut member completely formed from at least one electrically insulative material and including an outer surface and an inner surface, the inner surface forming a longitudinal lumen extending through the strut, a seal zone supporting protrusion extending from the outer surface of the strut member and upon which the seal zone element is mounted;

a contact supporting protrusion extending from the outer surface of the strut member, the contact supporting protrusion being longitudinally spaced apart from the seal zone supporting protrusion and upon which the contact element is mounted; and an insulative end cap mounted on an end of the strut, wherein a one of the contact and seal zone elements is held between the end cap and another of the contact and seal zone elements.

6. The lead of claim 5, wherein the strut end includes locking features fixedly engaging an inner surface of the end cap.

7. The lead of claim 6, wherein the locking features allow longitudinal play in a position of the engaged end cap.

8. The lead of claim 1, wherein an end of the strut includes a stop formed in the outer surfaces and wherein one of the contact element and the seal zone element is held between the stop and the other of the contact element and the seal zone element.

9. The lead of claim 5, wherein another end of the strut includes a stop formed in the outer surface and the contact element and the seal zone element are held between the end cap and the stop.

10. The lead of claim 5, wherein the end cap includes external features adapted to engage a connector sleeve extending from the proximal end of the lead.

11. The lead of claim 1, further comprising:

a connector pin; and a second elongate conductor extending from the lead proximal end into the connector, through the strut lumen, to couple with the connector pin;

wherein the strut lumen includes a portion engaging the connector pin.

12. The lead of claim 1, wherein the strut lumen includes a keying feature adapted to uniformly orient the strut member on an assembly pin.

13. The lead of claim 1, wherein the electrical contact element includes an outer surface and the seal zone element includes an outer surface approximately flush with the contact element outer surface.

14. The lead of claim 1, wherein:

the electrical contact element includes a recessed outer surface extending from an end of the contact element; and the seal zone element includes an inner surface overlapping the recessed surface of the contact element.

15. The lead of claim 1, wherein the seal zone element is formed from a polymer.

16. The lead of claim 15, wherein the polymer is selected from the group consisting of PEEK and polysulfone.

17. The lead of claim 1, wherein the seal zone element includes an outer surface free of protrusions exceeding a height of approximately 0.003 inch.

18. The lead of claim 1, wherein the seal zone element includes an outer surface free of protrusion exceeding a height of approximately 0.001 inch.

19. The lead of claim 1, wherein the seal zone element is formed from a polymer including one or more filler materials.

20. The lead of claim 19, wherein the one or more filler materials include glass fibers.

21. The lead of claim 19, wherein the polymer is selected from the group consisting of polysulfone and polyurethane.

22. The lead of claim 1, wherein the seal zone element is formed from a ceramic material.

23. The lead of claim 22, wherein the ceramic material is selected from the group consisting of alumina, sapphire and zirconia.

24. The lead of claim 1, wherein an end of the contact element is brazed to an adjacent end of the seal zone element.

25. The lead of claim 1, wherein the elongate conductor includes an insulative outer layer.

26. The lead of claim 25, wherein the insulative outer layer is formed from a fluoropolymer material.

27. The lead of claim 25, further comprising an adhesive backfill positioned between the seal zone element and the strut outer surface and wherein the elongate conductor passes through the adhesive backfill and the conductor insulative outer layer includes a surface treatment promoting adhesion to the adhesive backfill.

28. The lead of claim 1, further comprising:

one or more additional electrical contact elements and one or more additional seal zone elements positioned with the electrical contact element and the seal zone element to form an alternating array of contact elements and seal zone elements; and one or more additional elongate conductors extending from the lead proximal end into the connector, each coupled to a one of the one or more additional contact elements;

wherein the strut further comprises:

one or more additional seal zone supporting protrusions, each extending from the strut outer surface and upon which a one of the one or more additional seal zone elements is mounted, and one or more additional contact supporting protrusions, each extending from the strut outer surface and upon which a one of the one or more additional contact elements is mounted.

29. The lead of claim 28, wherein at least one of the seal zone supporting protrusions and at least one of the contact supporting protrusions each include a channel through which a one of the conductors passes.

30. The lead of claim 28, further comprising an adhesive backfill positioned beneath each seal zone element and the strut outer surface.

31. The lead of claim 30, wherein the strut further comprises a longitudinal channel facilitating application of the adhesive backfill from an end of the strut.

32. The lead of claim 30, wherein each seal zone element further includes an inner surface having a treatment promoting adhesion between the inner surface and the adhesive backfill.

33. The lead of claim 28, wherein an end of the strut includes a lead body-mounting surface.

34. The lead of claim 28, further comprising an Insulative end cap mounted on and end of the strut, wherein a one of the contact and seal zone elements is held between the end cap and another of the contact and seal zone elements.

35. The lead of claim 34, wherein the strut end includes locking features fixedly engaging an inner surface of the end cap.

36. The lead of claim 35, wherein the locking features allow longitudinal play in a position of the engaged end cap.

37. The lead of claim 28, wherein an end of the strut includes a stop formed in the outer surfaces, and wherein one of the contact element and the seal zone element is hold between the stop and the other of the contact element and the seal zone element.

38. The lead of claim 34, wherein another end of the strut includes a stop formed in the outer surface and each electrical contact element and each seal zone element is held between the stop and the end cap.

39. The lead of claim 34, wherein the end cap includes external features adapted to engage a connector sleeve extending from the lead proximal end.

40. The lead of claim 28, further comprising:

a connector pin; and a pin elongate conductor extending from the lead proximal end into the connector, through the strut lumen, to couple with the connector pin;

wherein the strut lumen includes a portion engaging the connector pin.

41. The lead of claim 28, wherein the strut lumen includes a keying feature adapted to uniformly orient the strut member on an assembly pin.

42. The lead of claim 28, wherein each electrical contact element includes an outer surface and each seal zone element includes an outer surface approximately flush with each contact element outer surface.

43. The lead of claim 28, wherein;

each electrical contact element includes a recessed outer surface extending from at least one end of each contact element; and each seal zone element includes an inner surface overlapping the recessed surface of an adjacent contact element.

44. The lead of claim 28, wherein one or more seal zone elements is formed from a polymer.

45. The lead of claim 44, wherein the polymer is selected from the group consisting of PEEK and polysulfone.

46. The lead of claim 28, wherein each seal zone element includes an outer surface free of protrusions exceeding a height of approximately 0.003 inch.

47. The lead of claim 28, wherein each seal zone element includes an outer surface free of protrusions exceeding a height of approximately 0.001 inch.

48. The lead of claim 28, wherein one or more seal zone elements is formed from a polymer including one or more filler materials.

49. The lead of claim 48, wherein the one or more filler materials include glass fibers.

50. The lead of claim 48, wherein The polymer is selected from the group consisting of polysulfone and polyurethane.

51. The lead of claim 28, wherein one or more seal zone elements is formed from a ceramic material.

52. The lead or adapter of claim 51, wherein the ceramic material is selected from the group consisting of alumina, sapphire and zirconia.

53. The lead or adapter of claim 28, wherein an end of each of one or more contact elements is brazed to an adjacent end of each of the one or more seal zone elements.

54. The lead of claim 28, wherein each elongate conductor includes an insulative outer layer.

55. The lead of claim 54, wherein the insulative outer layer is formed from a fluoropolymer material.

56. The lead of claim 55, further comprising an adhesive backfill positioned between each seal zone element and the strut outer surface and wherein each elongate conductor passes through the adhesive backfill and the conductor insulative outer layers include a surface treatment promoting adhesion to the adhesive backfill.

57. A medical electrical lead, comprising a connector coupled to a proximal end of the lead, the connector adapted to mate with a medical device and comprising:

an electrical contact element including an outer surface and an edge recessed from the outer surface and extending from an end of the contact element;

an elongate conductor extending from the proximal end of the lead into the connector where the conductor couples with the contact element;

a seal zone element positioned adjacent the contact element and including an inner surface overlapping the recessed edge of the contact element and an outer surface adapted to sealingly engage with an internal sealing ring of the medical device; the outer surface free of protrusions exceeding a height of approximately 0.003 inch and approximately flush with the outer surface of the contact element;

a relatively rigid strut member supporting the electrical contact element and the seal zone element; and an insulative end cap mounted on an end of the strut, wherein one of the contact element and the seal zone element is held between the end can and the other of the contact element and the seal zone element.

58. The lead of claim 57, wherein an end of the strut includes a lead body-mounting surface.

59. The lead of claim 57, wherein the strut end includes locking features fixedly engaging an inner surface of the end cap.

60. The lead of claim 57, wherein an end of the strut includes a stop, and wherein one of the contact element and the seal zone element is held between the stop and the other of the contact element and the seal zone element.

61. The lead of claim 57, wherein another end of the strut includes a stop and the contact element and The seal zone element are held between the end cap and the stop.

62. The lead of claim 57, wherein the end cap includes external features adapted to engage a connector sleeve extending from the proximal end of the lead.

63. The lead of claim 57, wherein the strut includes a longitudinal lumen extending therethrough and further comprising:

a connector pin; and a second elongate conductor extending from the lead proximal end into the connector, through the strut lumen, to couple with the connector pin;

wherein the strut lumen includes a portion engaging the connector pin.

64. The lead of claim 57, wherein the seal zone element is formed from a polymer.

65. The lead of claim 64, wherein the polymer is selected from the group consisting of PEEK and polysulfone.

66. The lead of claim 57, wherein the seal zone element is formed from a polymer including one or more filler materials.

67. The lead of claim 66, wherein the one or more filler materials includes glass fibers.

68. The lead of claim 66, wherein the polymer is selected from the group consisting of polysulfone and polyurethane.

69. The lead of claim 57, wherein the seal zone element is formed from a ceramic material.

70. The lead of claim 69, wherein the ceramic material is selected from the group consisting of alumina, sapphire and zirconia.

71. The lead of claim 57, wherein an end of the contact element is brazed to an adjacent end of the seal zone element in proximity to the recessed edge of the contact element.

72. A medical electrical connector terminal adapted to mate with a medical device and comprising:

an electrical contact element;

a seal zone element positioned adjacent the contact element;

a relatively rigid strut member completely formed from at least one electrically insulative material and including an outer surface and an inner surface, the inner surface forming a longitudinal lumen extending through the strut, a seal zone supporting protrusion extending from the outer surface of the strut member and upon which the seal zone element is mounted;

a contact supporting protrusion extending from the outer surface of the strut member, the contact supporting protrusion being longitudinally spaced apart from the seal zone supporting protrusion and upon which the contact element is mounted;

an adhesive backfill positioned beneath the seal zone element and the strut outer surface; and a longitudinal channel formed within the strut member facilitating application of the adhesive backfill from an end of the strut member.

73. The connector terminal of claim 72, wherein at least one of the seal zone and contact supporting protrusions includes a channel through which an elongated conductor passes to couple with the contact element.

74. The connector terminal of claim 72, wherein the seal zone element further includes an inner surface having a treatment promoting adhesion between the inner surface and the adhesive backfill.

75. The connector terminal of claim 72, wherein the strut includes a first end and a second end, the connector terminal further comprising an insulative end cap mounted on the first end of the strut, wherein one of the contact element and the seal zone element is held between the end cap and the other of the contact element and the seal zone element.

76. The connector terminal of claim 72, wherein the strut includes a first end and a second end, the first end including a stop formed in the outer surfaces, and wherein one of the contact element and the seal zone element is held between the stop and the other of the contact element and the seal zone element.

77. The connector terminal of claim 75, wherein the second end of the strut includes a stop formed in the outer surface and the contact element and the seal zone element are held between the end cap and the stop.

78. The connector terminal of claim 72, wherein the electrical contact element includes an outer surface and the seal zone element includes an outer surface approximately flush with the contact element outer surface.

79. The connector terminal of claim 72, wherein:

the electrical contact element includes a recessed outer surface extending from an end of the contact element; and the seal zone element includes an inner surface overlapping the recessed surface of the contact element.

80. The connector terminal of claim 72, wherein the seal zone element is formed of a polymer.

81. The connector terminal of claim 80, wherein the polymer is selected from the group consisting of PEEK and polysulfone.

82. The connector terminal of claim 72, wherein the seal zone element includes an outer surface free of protrusions exceeding a height of approximately 0.003 inch.

83. The connector terminal of claim 72, wherein the seal zone element includes an outer surface free of protrusion exceeding a height of approximately 0.001 inch.

84. The connector terminal of claim 72, wherein the seal zone element is formed from a polymer including one or more filler materials.

85. The connector terminal of claim 84, wherein the one or more filler materials include glass fibers.

86. The connector terminal of claim 84, wherein the polymer is selected from the group consisting of polysulfone and polyurethane.

87. The connector terminal of claim 72, wherein the seal zone element is formed from a ceramic material.

88. The connector terminal of claim 87, wherein the ceramic material is selected from the group consisting of alumina, sapphire and zirconia.

89. The lead of claim 72, wherein an end of the contact element is brazed to an adjacent end of the seal zone element.

* * * * *

UNITED STATES PATENT AND TRADEMARK OFFICE

CERTIFICATE OF CORRECTION

PATENT NO. : 7,108,549 B2
APPLICATION NO. : 10/812796
DATED : September 19, 2006
INVENTOR(S) : Suping Lyu et al.

It is certified that error appears in the above-identified patent and that said Letters Patent is hereby corrected as shown below:

Claim 3, Col. 8, line(s) 45, delete "The lead of claim 1 wherein . . ." and insert in place thereof -- The lead of claim 1, wherein . . . --

Claim 8, Col. 9, line(s) 16, delete ". . . outer surfaces and . . ." and insert in place thereof -- . . . outer surface, and . . . --

Claim 37, Col. 10, line(s) 62, delete ". . . outer surfaces, and . . ." and insert in place thereof -- . . . outer surface, and . . . --

Claim 76, Col. 13, line(s) 33, delete ". . . outer surfaces, and . . ." and insert in place thereof -- . . . outer surface, and . . . --

Signed and Sealed this

Second Day of June, 2009

JOHN DOLL

*Acting Director of the United States Patent and Trademark Office*